(12) United States Patent
Liu et al.

(10) Patent No.: US 11,274,275 B2
(45) Date of Patent: Mar. 15, 2022

(54) LACTOBACILLUS PARACASEI ET-22 AND USE THEREOF

(71) Applicant: INNER MONGOLIA YILI INDUSTRIAL GROUP CO., LTD, Inner Mongolia (CN)

(72) Inventors: Wei-Hsien Liu, Hohhot Inner Mongolia (CN); Wei-Lian Hung, Hohhot Inner Mongolia (CN); Ting Sun, Hohhot Inner Mongolia (CN); Ignatius Man-Yau Szeto, Hohhot Inner Mongolia (CN); Wen Zhao, Hohhot Inner Mongolia (CN)

(73) Assignee: Inner Mongolia Yili Industrial Group Co., Ltd., Hohhot Inner Mongolia (CN)

( * ) Notice: Subject to any disclaimer, the term of this patent is extended or adjusted under 35 U.S.C. 154(b) by 0 days.

(21) Appl. No.: 17/259,137

(22) PCT Filed: Sep. 23, 2019

(86) PCT No.: PCT/CN2019/107274
§ 371 (c)(1),
(2) Date: Jan. 8, 2021

(87) PCT Pub. No.: WO2020/063531
PCT Pub. Date: Apr. 2, 2020

(65) Prior Publication Data
US 2021/0253995 A1    Aug. 19, 2021

(30) Foreign Application Priority Data

Sep. 30, 2018 (CN) .......................... 201811147289.4
Sep. 30, 2018 (CN) .......................... 201811147290.7
Sep. 30, 2018 (CN) .......................... 201811164616.7

(51) Int. Cl.
C12N 1/20 (2006.01)
A61K 35/747 (2015.01)
(Continued)

(52) U.S. Cl.
CPC .............. *C12N 1/205* (2021.05); *A23K 10/18* (2016.05); *A23L 33/135* (2016.08); *A23L 33/40* (2016.08);
(Continued)

(58) Field of Classification Search
CPC .... A61K 2300/00; A61K 35/747; A61K 8/99; A61K 35/744; A61K 35/745;
(Continued)

(56) References Cited

U.S. PATENT DOCUMENTS 6,835,376 B1    12/2004  Neeser et al.
9,192,634 B2 *  11/2015  Castellana ............... A61K 8/99
(Continued)

FOREIGN PATENT DOCUMENTS

CN    101626774 A    1/2010
CN    102021127 A    4/2011
(Continued)

OTHER PUBLICATIONS

Widipedia Exhibit, pp. 1-7. (Year: 2021).*
(Continued)

*Primary Examiner* — David W Berke-Schlessel
(74) *Attorney, Agent, or Firm* — Knobbe Martens Olson & Bear, LLP (57) ABSTRACT

The present application relates to a *Lactobacillus paracasei* ET-22 strain and use thereof. The present application provides a *Lactobacillus paracasei* ET-22 strain with a deposit number of CGMCC No. 15077, a composition containing the strain and a method of treating a subject using the strain. The present application also relates to a method for treating (Continued)

a subject, including administering an effective amount of the *Lactobacillus paracasei* ET-22 strain to a subject in need thereof for 1) whitening teeth and/or inhibiting oral pathogens; 2) adjusting balance of flora in the subject; 3) promoting growth of bifidobacteria and/or lactic acid bacteria; and/or 4) enhancing immunity of the subject.

14 Claims, 5 Drawing Sheets

(51) Int. Cl.
| | |
|---|---|
| C11D 3/38 | (2006.01) |
| A61K 8/96 | (2006.01) |
| A61Q 11/00 | (2006.01) |
| A23L 33/135 | (2016.01) |
| A23L 33/00 | (2016.01) |
| A23K 10/18 | (2016.01) |
| C12R 1/225 | (2006.01) |

(52) U.S. Cl.
CPC ............. *A61K 8/96* (2013.01); *A61K 35/747* (2013.01); *A61Q 11/00* (2013.01); *C11D 3/381* (2013.01); *A23V 2002/00* (2013.01); *A23Y 2220/63* (2013.01); *C12R 2001/225* (2021.05)

(58) Field of Classification Search
CPC .. A61K 35/742; A61K 31/196; A61K 31/198; A61K 31/205; A61K 31/365; A61K 31/405; A61K 31/472; A61K 31/51; A61K 31/519; A61K 31/525; A61K 31/7048; A61K 31/714; A61K 36/064; A61K 36/28; A61K 36/48; A61K 36/484; A61K 36/66; A61K 45/06; A61K 2035/115; A61K 2800/5922; A61K 2800/87; A61K 2800/92; A61K 31/047; A61K 31/145; A61K 31/33; A61K 31/47; A61K 31/7028; A61K 35/748; A61K 8/044; A61K 8/11; A61K 8/22; A61K 8/345; A61K 8/44; A61K 8/445; A61K 8/466; A61K 8/4926; A61K 8/60; A61K 8/602; A61K 8/67; A61K 8/673; A61K 8/92; A61K 8/9728; A61K 8/9789; A61K 9/0056; A61K 9/006; A23V 2002/00; A23V 2200/312; A23V 2200/3204; A23V 2200/324; A61Q 11/00; A61Q 17/005; A61Q 19/00; A61P 1/02; A61P 31/04; A61P 31/10; A61P 31/00; A61P 31/02; A61P 11/00; A61P 31/12; A61P 37/02; A23L 33/135; A23L 2/52; A23L 33/105; A23L 33/15; A23L 33/175; A23L 33/40; A61C 19/063; A61C 19/066; A61C 15/02; A61C 15/041; C12N 1/20; C12N 1/205; C12N 2001/24; C12R 2001/25; C12R 1/225; A23Y 2220/63; A23Y 2220/03; A23Y 2220/39; A23Y 2220/71; A23Y 2220/73; A23Y 2220/79; A23Y 2240/49; A23P 10/35
See application file for complete search history.

(56) References Cited

U.S. PATENT DOCUMENTS

| | | | | |
|---|---|---|---|---|
| 9,511,102 | B2 * | 12/2016 | Castellana | ............. A61Q 11/00 |
| 9,636,196 | B2 * | 5/2017 | Hillman | ............... A61C 19/066 |
| 2008/0193427 | A1 | 8/2008 | Kaesler et al. | |
| 2009/0311199 | A1 * | 12/2009 | Hillman | .................... A61P 1/02 |
| | | | | 424/50 |
| 2011/0038837 | A1 | 2/2011 | Nishida et al. | |
| 2012/0128644 | A1 * | 5/2012 | Hillman | .................. A61P 31/10 |
| | | | | 424/93.44 |
| 2012/0128645 | A1 | 5/2012 | Nikawa | |
| 2013/0209374 | A1 * | 8/2013 | Cune | ......................... C12N 1/20 |
| | | | | 424/48 |
| 2013/0224252 | A1 | 8/2013 | Hara et al. | |
| 2015/0273000 | A1 * | 10/2015 | Castellana | ............... C12N 1/20 |
| | | | | 424/93.45 |
| 2016/0114024 | A1 | 4/2016 | Tanaka et al. | |
| 2017/0028001 | A1 | 2/2017 | Grompone et al. | |
| 2017/0245973 | A1 * | 8/2017 | Hillman | .................... A61P 1/02 |
| 2017/0319315 | A1 * | 11/2017 | Hillman | .................... A61P 1/02 |
| 2018/0206541 | A1 * | 7/2018 | Hsieh | ..................... A61K 45/06 |
| 2019/0000757 | A1 | 1/2019 | Santas Gutiérrez et al. | |
| 2019/0290705 | A1 | 9/2019 | Wade | |
| 2020/0016065 | A1 * | 1/2020 | Koski | ....................... A61K 8/60 |
| 2020/0100536 | A1 * | 4/2020 | Hsieh | ...................... A61K 8/99 |
| 2021/0000890 | A1 * | 1/2021 | Shemesh | ................. A61K 8/345 |
| 2021/0085729 | A1 * | 3/2021 | Farber | .................. A61K 8/4926 |

FOREIGN PATENT DOCUMENTS

| | | |
|---|---|---|
| CN | 102470151 A | 5/2012 |
| CN | 103070287 A | 5/2013 |
| CN | 103179975 A | 6/2013 |
| CN | 104523762 A | 4/2015 |
| CN | 104894021 A | 9/2015 |
| CN | 105579574 A | 5/2016 |
| CN | 106604736 A | 4/2017 |
| CN | 107916236 A | 4/2018 |
| CN | 107920986 A | 4/2018 |
| CN | 108148784 A | 6/2018 |
| CN | 108338361 A | 7/2018 |
| CN | 108603165 A | 9/2018 |
| JP | 2014000039 A | 1/2014 |
| WO | WO 2000053200 A1 | 9/2000 |
| WO | WO 2006027265 A1 | 3/2006 |

OTHER PUBLICATIONS

Teanpaisan, Rawee; et al.; "Effect of Long-Term Consumption of Lactobacillus paracasei SD1 on Reducing Mutans *Streptococci* and Caries Risk: A Randomized Placebo-Controlled Trial" Dentistry Journal, 3, 43-54, 2015 (Year: 2015).*
Lu, Hongyun; etal; "Safety Evaluation of Bifidobacterium lactis BL-99 and Lacticaseibacillus paracasei K56 and ET-22 in vitro and in vivo" Frontiers in Microbiology, 12, 1-14, 2021 (Year: 2021).*
"Guidelines for the Evaluation of Probiotics in Food: Report of a Joint FAO/WHO Working Group on Drafting Guidelines for the Evaluation of Probiotics in Food", London Ontario, Canada Apr. 30 and May 1, 2002: 1-7.
Li, "Application of probiotics for dental caries prevention in children" Prevention and treatment of oral diseases, 2016, vol. 24, No. 9, pp. 558-560.
Office Action issued in Chinese Application No. CN 201811147290. 7, dated Nov. 19, 2020.
Office Action issued in Chinese Application No. CN 201811147289. 4, dated Nov. 20, 2020.
Office Action issued in Chinese Application No. CN 201811164616. 7, dated Dec. 1, 2020.
Teanpaisan et al., "Inhibitory effect of oral *Lactobacillus* against oral pathogens" Letters in Applied Microbiology, 53, 2011, pp. 452-459.
Tsai et al., "Time-dependent persistence of enhanced immune response by a potential probiotic strain *Lactobacillus paracasei* subsp.*paracasei* NTU 101" International Journal of Food Microbiology, 128, 2008, pp. 219-225.
International Search Report issued in PCT Application No. PCT/CN2019/107274, dated Feb. 4, 2020.
Extended European Search Report issued in EP Application No. 19865158.0, dated Jul. 21, 2021.

(56) References Cited

OTHER PUBLICATIONS

Ou et al., "Heat-Killed Lactic Acid Bacteria Enhance Immunomodulatory Potential by Skewing Immune Response toward Th1 Polarization", Journal of Food Science, 75(5): M260-M267 (2011).
Yang et al., "The Prebiotic Activity of Simulated Gastric and Intestinal Digesta of Polysaccharides from the *Hericium erinaceus*", Molecules, 23(3158): 1-14 (2018).

* cited by examiner

*LACTOBACILLUS PARACASEI* ET-22 AND USE THEREOF

FIELD

The present disclosure relates to the technical field of microorganisms, and in particular to *Lactobacillus paracasei* and the use thereof, for example for promoting the growth of bifidobacteria and lactic acid bacteria, promoting the humoral immunity and the killing activity of NK cell, and suppressing oral pathogens.

BACKGROUND

1. Probiotics and Probiotic Products

Probiotics refer to viable microorganisms that can be added to a composition while maintaining the activity and exert physiological effects on subjects who ingest the composition containing the probiotics. The World Health Organization defines probiotic products as food containing a sufficient number of viable microorganisms, and after each process of food processing and entering the human intestine, still maintaining an appropriate number of and activity of the viable microorganisms. Therefore, the product should be able to maintain a relatively stable number of viable microorganisms after the production of microorganism powder, the production and processing of the product, and after experiencing the stress of stomach acid and bile salt in the human gastrointestinal tract.

2. Probiotics and Intestinal Flora Imbalance

The balance of intestinal flora is closely related to human health. The intestinal flora includes beneficial bacteria, neutral bacteria and harmful bacteria. In healthy human intestines, beneficial bacteria occupy an advantageous position, and interact with harmful bacteria continuously to maintain human health. If the beneficial bacteria in the intestine are reduced due to various factors, harmful bacteria will multiply in large quantities, and the microecological balance in the intestine will be broken, causing various clinical symptoms such as enteritis and diarrhea. In additional, a large number of antibiotics are usually used clinically. Although they can effectively kill harmful bacteria, they also kill beneficial bacteria, causing intestinal flora imbalance and causing diseases.

For those with intestinal flora disorders, oral administration of probiotics is a direct and effective way to regulate intestinal flora. Oral administration of probiotic preparations or probiotic-containing products can directly or indirectly adjust the composition of the intestinal flora, activate the endogenous microbiota or immune system activity of the host to achieve probiotic effects.

3. Probiotics and Immune Function

Immunity is an important physiological function of the human body, and includes non-specific immunity and specific immunity. Non-specific immunity does not require pre-exposure to antigens, and once pathogens enter the body, they will quickly eliminate the pathogens. Both phagocytes and natural killer cells have clearing and killing effects and are important members of the non-specific immune system. Specific immunity involves immune cells (T lymphocytes and B lymphocytes) that specifically recognize foreign bodies and have an immune memory ability. The most important information transducers between the immune systems are cytokines. Each cytokine has different stimulating functions for different cell types. They bind to specific receptors on the surface of cell to induce cell growth and functional activity. The human body relies on this function to recognize the "self" and "non-self" components, thereby destroying and repelling the antigenic substances entering the body or the damaged cells and tumor cells produced by the human body to maintain the health of the human body, resist or prevent the infection of microorganisms or parasites or the invasion of other undesirable organisms.

Enhancing immunity of the body is a common demand of children, adolescents, adults and elderly people of all ages and all social classes. Studies have shown that a variety of human diseases such as colds, enteritis and joint inflammation are all related to low immunity. Probiotics have many functions, such as regulating intestinal flora imbalance, enhancing intestinal immune function, and inhibiting allergic reactions. The research on the immunomodulatory effects of probiotics shows that probiotics can promote both specific and non-specific immunity to promote human health. Therefore, a problem to be solved by the present disclosure is to screen for probiotics with immunity-enhancing properties.

4. Probiotics and Oral Hygiene

The health care of infant deciduous teeth will affect the permanent teeth in the future. Therefore, oral cleanliness is very important from infancy. If bacteria grow in the mouth, they will easily adhere to the gum surface, and after the deciduous teeth grow, they will directly attach to the baby's deciduous teeth and cause caries. Deciduous teeth are the foundation of all teeth, and can maintain appropriate space and distance for the growth of permanent teeth in the future. If deciduous teeth are not well taken care of and caries occur in the deciduous teeth, dental caries will cause serious loss of the space, and when permanent teeth develop in the future, the permanent teeth will be surrounded by bacteria and pustules, resulting in new teeth that are more likely to have dental caries, and even affect the incidence of periodontal disease in adulthood and old age.

General edible products containing lactic acid bacteria (LAB) only have the effect of adjusting intestinal health. Although tens of thousands of strains of lactic acid bacteria exist in nature, only a few strains have been found to have the potential qualities to maintain oral health and whiten teeth. The ability of these strains to inhibit oral pathogens and adsorb to oral mucosal epidermal cells, and whether they can still maintain the ability to inhibit pathogens and produce hydrogen peroxide in dental products, are important basis for stimulating bacterial strains to exhibit functions in the oral cavity, controlling the microecological balance in the oral cavity, and screening functional strains for maintaining oral health and whitening teeth.

The literature shows that probiotics can compete with pathogenic bacteria for the survival area and nutrition, promote the aggregation of the pathogenic bacteria, and secrete bacteriostatic substances that make the pathogenic bacteria weaker or even kill the pathogenic bacteria. Therefore, they have the ability of reducing the number of oral pathogens, maintaining oral health, as well as secreting hydrogen peroxide to remove oral odor and whiten teeth.

To date, only a few strains of lactic acid bacteria have been found to have the active effect of maintaining oral health and whitening teeth through experimental processes. The function of lactic acid bacteria for health lies in the specificity of strains rather than species. Such strains with special effects on human health are called functional probiotics (Guidelines for the evaluation of probiotics in food; Report of joint FAO/WHO working group on drafting guidelines for the evaluation of probiotics in food; London Ontario, Canada April 30 and May 1, 2002: 1-7).

In summary, the development of functional probiotics with beneficial activity is the current goal.

SUMMARY OF THE INVENTION

The inventors found that the ET-22 strain (with deposit number CGMCC No. 15077) as a single strain has a variety of beneficial activities, including, for example, significantly promoting the growth of intestinal bifidobacteria and lactic acid bacteria, tolerating the simulated gastrointestinal fluid stress environment in vitro; significantly enhancing humoral immunity and activating NK cell, including, for example, increasing the number of antibody-producing cells and the half hemolysis concentration $HC_{50}$, activating NK cell, improving weakened immune system caused by irregular diet and increased work pressure; inhibiting oral pathogens and producing peroxide to for example whiten teeth. Experiments show that the strain has no acute oral toxicity, no antibiotic resistance, and is safe for food processing.

Therefore, the present disclosure provides *Lactobacillus paracasei* with beneficial activity and uses thereof.

In some embodiments, the present disclosure relates to the following items, but is not limited thereto.

1. A *Lactobacillus paracasei* ET-22 strain, which is deposited in the China General Microbiological Culture Collection Center (CGMCC), with the deposit date of Dec. 18, 2017, and the deposit number CGMCC No. 15077.

2. A composition comprising the *Lactobacillus paracasei* ET-22 strain of item 1, and an excipient, a diluent and/or a carrier.

3. The composition of item 2, wherein the composition is a food composition, a pharmaceutical composition, or an oral cleaning composition.

4. The composition of item 2, wherein the ET-22 strain is an active strain and/or a deactivated strain.

5. The composition of item 3, wherein the composition is a food composition, and the excipient, diluent and/or carrier includes dairy drinks, tea, coffee, chewing gum and dentifrice, jerky for pet food or a combination thereof.

6. The composition of item 3, wherein the composition is an oral cleaning composition, and the excipient, diluent and/or carrier is toothpaste, tooth powder, mouthwash, breath freshener spray, fluorine-coating agent, denture cleaner, pet tooth cleaning gum or pet laxatone, tooth brush, interdental brush, dental floss, oral swab or pet tooth cleaning bone.

7. The composition of item 3, wherein the composition is a pharmaceutical composition, which 1) is formulated in an oral dosage form; 2) includes a therapeutic and/or prophylactic composition; 3) includes a nutritional composition; 4) is a dry or wet preparation; or 5) is formulated into a gel, cream, spray, aerosol, ointment, emulsion, suspension, patch, buccal tablet or sublingual tablet.

8. The composition of item 2, wherein the composition is used for 1) whitening teeth and/or inhibiting oral pathogens; 2) adjusting the balance of flora in a subject; 3) promoting growth of bifidobacteria and/or lactic acid bacteria; and/or 4) enhancing immunity of a subject, for example, enhancing humoral immunity and/or cellular immunity of the subject, for example, increasing the number of antibody-producing cells, increasing half hemolysis concentration $HC_{50}$ and/or increasing the activity of NK cells.

9. The composition of item 2, wherein the composition is administered to a subject such as a mammalian subject, via a gastrointestinal route.

10. The composition of item 2, wherein the content of the ET-22 strain in the composition is equal to or more than $10^6$ CFU, such as equal to or more than $10^7$ CFU, equal to or more than $10^8$ CFU, equal to or more than $10^9$ CFU, equal to or more than $10^{10}$ CFU, or equal to or more than $10^{11}$ CFU.

11. A method for treating a subject, comprising administering an effective amount of the *Lactobacillus paracasei* ET-22 strain of item 1 to a subject in need thereof for 1) whitening teeth and/or inhibiting oral pathogens; 2) adjusting balance of flora in the subject; 3) promoting growth of bifidobacteria and/or lactic acid bacteria; and/or 4) enhancing immunity of the subject, for example, enhancing humoral immunity and/or cellular immunity of the subject, for example, increasing the number of antibody-producing cells, increasing half hemolysis concentration $HC_{50}$ and/or increasing the activity of NK cells.

12. The method of item 11, wherein the ET-22 strain is in the form of the composition of item 2.

13. The method of item 11, wherein the ET-22 strain is an active strain and/or a deactivated strain.

14. The method of item 11, wherein the ET-22 strain is administered to a subject, such as a mammalian subject, via a gastrointestinal route.

15. The method of item 11, wherein the ET-22 strain is administered to the subject in an amount of equal to or more than $10^6$ CFU, such as equal to or more than $10^7$ CFU, equal to or more than $10^8$ CFU, equal to or more than $10^9$ CFU, equal to or more than $10^{10}$ CFU, or equal to or more than $10^{11}$ CFU.

In some embodiments, the present disclosure provides a culture comprising the *Lactobacillus paracasei* ET-22 strain. In some embodiments, the culture may also comprises a suitable lactic acid bacteria medium. In some embodiments, the lactic acid bacteria medium includes a solid medium and a liquid medium, such as MRS medium. In some embodiments, the culture includes a freeze-dried culture of the *Lactobacillus paracasei* ET-22 strain.

In some embodiments, the present disclosure provides a method for regulating balance of flora in a subject, the method comprising administering the *Lactobacillus paracasei* ET-22 strain to the subject to adjust the balance of flora.

In some embodiments, the present disclosure provides a method for enhancing immunity in a subject, the method comprising administering the *Lactobacillus paracasei* ET-22 strain to the subject to enhance the immunity. In some embodiments, the present disclosure provides a method for increasing the number of antibody-producing cells, increasing half hemolysis concentration $HC_{50}$ and/or increasing activity of NK cells in a subject, the method comprising administering the *Lactobacillus paracasei* ET-22 strains to the subject. In some embodiments, the humoral immunity and/or cellular immunity of the subject is enhanced by the method of the present disclosure. In some embodiments, the number of antibody-producing cells in the subject is increased by the method.

In some embodiments, the present disclosure provides a method for whitening teeth and/or inhibiting oral pathogens and/or treating infectious diseases caused by oral pathogens in a subject, the method comprising administering the *Lactobacillus paracasei* ET-22 strain to the subject. In some embodiments, the present disclosure provides a method for treating diseases such as caries, tooth decay, periodontal disease such as periodontitis, halitosis in a subject, the method comprising administering the *Lactobacillus paracasei* ET-22 strain to the subject. In some embodiments, the *Lactobacillus paracasei* ET-22 strain may be provided to the subject in the form of composition such as a food composition, an oral cleaning composition, and a pharmaceutical composition. In some embodiments, the present disclosure provides a method for inhibiting oral pathogens and/or treating infectious diseases caused by oral pathogens, including *Streptococcus mutans, Fusobacterium nucleatum* (including subsp. *polymorphum), Aggregatibacter actinomycetemcomitans* and *Porphyromonas gingivalis.*

In some embodiments, the strain is an active strain. In some embodiments, the strain can be administered to the subject via the gastrointestinal route. In some embodiments, the strain can be administered to the subject orally. In some embodiments, the strain is administered to the subject by other means suitable for intestinal absorption, for example, by means such as a feeding tube without passing through the mouth, throat and esophagus.

In some embodiments, the subject may be a mammal. In some embodiments, the subject may be a mammal, such as a human, monkey, horse, cow, dog, cat, mouse, rat, pig, and the like.

In some embodiments, the method and composition of the present disclosure promote the growth of bifidobacteria and lactic acid bacteria.

In some embodiments, the growth of intestinal bacteria such as *Enterobacter* is not affected after the administration of the method and composition of the present disclosure.

In some embodiments, the present disclosure provides a method of promoting the growth of bifidobacteria and/or lactic acid bacteria in a subject, the method comprising administering the *Lactobacillus paracasei* ET-22 strain to the subject to promote the growth of bifidobacteria and/or lactic acid bacteria.

In some embodiments, the growth of intestinal bacteria such as *Enterobacter* is not affected after the administration of the method and composition of the present disclosure.

In some embodiments, the composition of the present disclosure may be in any composition form suitable for use, for example, a food (including beverage) composition, a pharmaceutical composition or an oral cleaning composition. In some embodiments, the food composition, pharmaceutical composition or oral cleaning composition is a composition for the oral cavity, such as a food composition, a pharmaceutical composition or an oral cleaning composition for whitening teeth and/or inhibiting oral pathogens. In some embodiments, the composition containing the lactic acid bacteria strain of the present disclosure has the function of whitening teeth and/or inhibiting oral pathogens, and exists in the form of a food composition, an oral cleaning composition or a pharmaceutical composition.

In some embodiments, the composition may comprise a suitable excipient, diluent and/or carrier, such as physiologically or pharmaceutically acceptable excipient, diluent and/or carrier.

In some embodiments, the composition may be a food composition. In some embodiments, the excipient, diluent and/or carrier may be a food. In some embodiments, the food may include beverages such as cereal products, oils, meat products, dairy products, aquatic products, canned foods, sugary foods, cold foods, alcoholic beverages, pet foods, and the like. In some embodiments, the food may include beverages such as dairy drinks, tea, coffee, chewing gum and dentifrice, jerky for pet food or a combination thereof.

In some embodiments, the composition may be a pharmaceutical composition. In some embodiments, the composition may be formulated as an oral dosage form or a topical dosage form. In some embodiments, the composition may comprise a therapeutic and/or prophylactic composition. In some embodiments, the composition may be a nutritional composition. In some embodiments, the composition can be formulated as a dry or wet preparation. In some embodiments, the composition may be prepared as a gel, cream, spray, aerosol, ointment, emulsion, suspension, patch, buccal tablet or sublingual tablet.

In some embodiments, the composition may be an oral cleaning composition. In some embodiments, the excipient, diluent and/or carrier may be toothpaste, tooth powder, mouthwash, breath freshener spray, fluoride agent, denture cleaner, pet tooth cleaning gum or pet laxatone. In some embodiments, the excipient, diluent and/or carrier is a tooth brush, interdental brush, dental floss, oral swab or pet tooth cleaning bone. In some embodiments, in addition, the composition may be a solid, powder, or paste oral hygiene composition. In some embodiments, the composition may be toothpaste, chewing gum, candy, liquid mouthwash such as collutory, and the like.

In some embodiments, the composition of the present disclosure can be used as a probiotic and/or prebiotic composition, a pharmaceutical composition for treating oral infections, or a functional food. In some embodiments, the *Lactobacillus paracasei* ET-22 strain has activity to inhibit oral pathogens. In some embodiments, probiotics may refer to viable microorganisms that can be added to a composition such as foods (such as milk, cheese), medicines (such as capsules, tablets, pills, powders, etc.) or oral hygiene products and the like while maintaining the activity and exert physiological effects on subjects who ingest the composition containing the probiotics. Prebiotics may refer to substances that are added to a composition such as foods (such as milk, cheese), medicines (such as capsules, tablets, pills, powders, etc.) or oral hygiene products and the like, to act on the components of the microbiota, facilitate the establishment of beneficial bacteria and/or hinder the establishment of pathogenic bacteria. In some embodiments, the strain of the present disclosure can be prepared in the form of probiotics or prebiotics.

In some embodiments, the pharmaceutical composition includes an oral dosage form or a topical dosage form.

In some embodiments, the excipient or diluent of the oral cleaning composition is toothpaste, tooth powder, mouthwash, breath freshener spray, fluoride agent, denture cleaner, pet tooth cleaning gum or pet laxatone.

In some embodiments, the carrier is a tooth brush, interdental brush, dental floss, oral swab or pet tooth cleaning bone.

In some embodiments, the present disclosure provides a food composition, an oral cleaning composition, and a pharmaceutical composition containing the strain of lactic acid bacteria, which can inhibit the growth of oral pathogens to maintain oral health.

In the composition of the present disclosure, the strain may be present in an effective amount. For example, the content of the lactic acid bacteria strain in the composition may be equal to or more than $10^6$ CFU, such as equal to or more than $10^7$ CFU, equal to or more than $10^8$ CFU, equal to or more than $10^9$ CFU, equal to or more than $10^{10}$ CFU, or equal to or more than $10^{11}$ CFU; preferably, the content of the strain is equal to or more than $10^9$ CFU.

In some embodiments, it has been found that the effects of probiotics for promoting the growth of bifidobacteria and/or lactic acid bacteria and/or adjusting the flora balance are strain-specific. It has been found that the *Lactobacillus paracasei* ET-22 strain has an excellent effect for promoting the growth of bifidobacteria and/or lactic acid bacteria and/or adjusting the flora balance, compared with a control without the strain or a control strain such as other *Lactoba-*

*cillus* strains (such as the ordinary *Lactobacillus paracasei* strain). In some embodiments, the *Lactobacillus paracasei* ET-22 strain has an increased effect for promoting the growth of bifidobacteria and/or lactic acid bacteria and/or adjusting the flora balance, compared with a control without the strain or a control strain such as other *Lactobacillus* strains (such as the ordinary *Lactobacillus paracasei* strain). In some embodiments, the *Lactobacillus paracasei* ET-22 strain is able to promote the growth of bifidobacteria and/or lactic acid bacteria and/or improve the flora balance of a subject (for example, by 10%, 20%, 30%, 40%, 50%, 60%, 70%, 80%, 90%, 100%, 2 folds, 3 folds, 4 folds, 5 folds, 6 folds, 7 folds, 8 folds, 9 folds, 10 folds or more folds), compared with a control without the strain or a control strain such as other *Lactobacillus* strains (such as the ordinary *Lactobacillus paracasei* strain). In some embodiments, the promotion of the growth of bifidobacteria and/or lactic acid bacteria and/or the adjustment of the flora balance in the subject can be measured by methods known in the art. In some embodiments, the promotion of the growth of bifidobacteria and/or lactic acid bacteria and/or the adjustment of the flora balance in a subject can be measured, for example, by comparing the changes in bifidobacteria, lactic acid bacteria, enterococci, and enterobacteria within and between groups before and after the experiment. In some embodiments, the *Lactobacillus paracasei* ET-22 strain can be used to manufacture a composition and/or kit for promoting the growth of bifidobacteria and/or lactic acid bacteria and/or adjusting the flora balance in a subject. In some embodiments, the composition and/or kit for promoting the growth of bifidobacteria and/or lactic acid bacteria and/or adjusting the flora balance in a subject may also comprise other substances suitable for promoting the growth of bifidobacteria and/or lactic acid bacteria and/or adjusting the flora balance in a subject.

In some embodiments, it has been found that the *Lactobacillus paracasei* ET-22 strain has the ability of inhibiting oral pathogens, such as caries bacteria, gingival bacteria, and oral odor bacteria. In addition, *Lactobacillus paracasei* ET-22 strain can secrete hydrogen peroxide, which in addition to inhibiting oral pathogens, has the effect of whitening teeth. In some embodiments, the *Lactobacillus paracasei* ET-22 strain has excellent immunomodulation effect, compared with a control without the strain or a control strain such as other *Lactobacillus* strains (such as the ordinary *Lactobacillus paracasei* strain). In some embodiments, the *Lactobacillus paracasei* ET-22 strain has the effect of improving the humoral and/or cellular immunity of a subject, compared with a control without the strain or a control strain such as other *Lactobacillus* strains (such as the ordinary *Lactobacillus paracasei* strain). In some embodiments, the *Lactobacillus paracasei* ET-22 strain is able to improve the humoral and/or cellular immunity of a subject (for example, by 10%, 20%, 30%, 40%, 50%, 60%, 70%, 80%, 90%, 100%, 2 folds, 3 folds, 4 folds, 5 folds, 6 folds, 7 folds, 8 folds, 9 folds, 10 folds or more folds), compared with a control without the strain or a control strain such as other *Lactobacillus* strains (such as the ordinary *Lactobacillus paracasei* strain). In some embodiments, the improvement of the humoral and/or cellular immunity of a subject can be measured by methods known in the art, for example, by determining the antibody-producing cell, the half hemolysis concentration $HC_{50}$, and the activity of NK cells. In some embodiments, the *Lactobacillus paracasei* ET-22 strain can be used to manufacture a composition and/or kit for enhancing the immunity of a subject. In some embodiments, the composition and/or kit for enhancing the immunity of a subject may further comprise other substances suitable for enhancing the immunity.

In some embodiments, it has been found that the *Lactobacillus paracasei* ET-22 strain has an excellent inhibitory effect on oral pathogens, compared with a control without the strain or a control strain such as other *Lactobacillus* strains (such as the ordinary *Lactobacillus paracasei* strain). In some embodiments, the *Lactobacillus paracasei* ET-22 strain has the ability of producing peroxide to whiten teeth, compared with a control without the strain or a control strain such as other *Lactobacillus* strains (such as the ordinary *Lactobacillus paracasei* strain). In some embodiments, the *Lactobacillus paracasei* ET-22 strain is capable of inhibiting one or more of the following oral pathogens or has improved inhibitory activity (for example, by 10%, 20%, 30%, 40%, 50%, 60%, 70%, 80%, 90%, 100%, 2 folds, 3 folds, 4 folds, 5 folds, 6 folds, 7 folds, 8 folds, 9 folds, 10 folds or more folds), compared with a control without the strain or a control strain such as other *Lactobacillus* strains (such as the ordinary *Lactobacillus paracasei* strain): *Streptococcus mutans, Fusobacterium nucleatum* (including subsp. *polymorphum*), *Aggregatibacter actinomycetemcomitans* and *Porphyromonas gingivalis*. In some embodiments, the *Lactobacillus paracasei* ET-22 strain is capable of inhibiting all oral pathogens or has improved inhibitory activity (for example, by 10%, 20%, 30%, 40%, 50%, 60%, 70%, 80%, 90%, 100%, 2 folds, 3 folds, 4 folds, 5 folds, 6 folds, 7 folds, 8 folds, 9 folds, 10 folds or more folds), compared with a control without the strain or a control strain such as other *Lactobacillus* strains (such as the ordinary *Lactobacillus paracasei* strain): *Fusobacterium nucleatum* (including subsp. *polymorphum*), *Aggregatibacter actinomycetemcomitans* and *Porphyromonas gingivalis*. In some embodiments, the *Lactobacillus paracasei* ET-22 strain is particularly capable of inhibiting the following oral pathogens or has better inhibitory activity (for example, by 10%, 20%, 30%, 40%, 50%, 60%, 70%, 80%, 90%, 100%, 2 folds, 3 folds, 4 folds, 5 folds, 6 folds, 7 folds, 8 folds, 9 folds, 10 folds or more folds), compared with a control without the strain or a control strain such as other *Lactobacillus* strains (such as the ordinary *Lactobacillus paracasei* strain): *Streptococcus mutans, Fusobacterium nucleatum* (including subsp. *polymorphum*), *Aggregatibacter actinomycetemcomitans* and *Porphyromonas gingivalis*. In some embodiments, the pharmaceutical composition can be used to treat diseases such as caries, tooth decay, periodontal diseases such as periodontitis, halitosis, and the like. In some embodiments, the *Lactobacillus paracasei* ET-22 strain can be used to manufacture a composition and/or kit for whitening teeth and/or treating oral diseases. In some embodiments, the composition and/or kit for whitening teeth and/or treating oral diseases may further comprise other substances suitable for whitening teeth and/or treating oral diseases.

In some embodiments, the present disclosure provides a method of preparing a composition such as a food composition, a pharmaceutical composition, or an oral cleaning composition, the method comprising adding the *Lactobacillus paracasei* ET-22 strain to the composition.

The purpose, technical content, features, and the technical effect of the present disclosure can be more easily understood through the following detailed description of specific examples in combination with the drawings

[Preservation of Biomaterials]

The *Lactobacillus paracasei* ET-22 strain of the present disclosure is deposited in the China General Microbiological Culture Collection Center (CGMCC), with the deposit date of Dec. 18, 2017, and the deposit number CGMCC No. 15077; the address of the depositary unit is Institute of Microbiology, Chinese Academy of Sciences, No. 3, Courtyard No. 1, Beichenxi Road, Chaoyang District, Beijing, China.

The *Lactobacillus paracasei* K56 strain is deposited in the China General Microbiological Culture Collection Center (CGMCC), with the deposit date of Dec. 29, 2017, and the deposit number CGMCC No. 15139; the address of the depositary unit is Institute of Microbiology, Chinese Academy of Sciences, No. 3, Courtyard No. 1, Beichenxi Road, Chaoyang District, Beijing, China.

DETAILED DESCRIPTION OF THE PREFERRED EMBODIMENT

Unless otherwise specifically defined, all technical and scientific terms used herein have the same meaning as commonly understood by those of ordinary skill in the relevant field.

The freeze-dried culture of the lactic acid bacteria strain according to the present disclosure has been deposited in China Center for Type Culture Collection and the China General Microbiological Culture Collection Center. The details of the deposit are shown in the table below:

TABLE 1

Deposit information of the lactic acid bacteria strain

| Strain name | Classification | Deposit number | Deposit date |
|---|---|---|---|
| ET-22 | *Lactobacillus paracasei* | CGMCC 15077 | Dec. 18, 2017 |

Morphology and General Properties of the Lactic Acid Bacteria Strain

The taxonomic characteristics of the strain are confirmed by 16S rDNA sequence analysis and API bacterial identification system analysis results. The morphological and general characteristics of the above strain are detailed in the table below:

TABLE 2

Morphology and general characteristics of the lactic acid bacteria strain

| Strain name | Morphological characteristics |
|---|---|
| *Lactobacillus paracasei* ET-22 strain | 1. When cultured in MRS medium, the strain is short and medium rod-shaped, with rounded ends, usually chain-shaped and occasionally appear in pairs. 2. Gram-positive bacilli, does not produce spores, has no catalase, oxidase and motility, can grow in both aerobic and anaerobic environments, the most suitable growth temperature being 37° ± 1° C., facultative heterogeneous fermentation, does not produce gas during glucose metabolism. |

The fermentation conditions of this strain are as follows:

MRS liquid medium: peptone, 10.0 g; beef extract, 10.0 g; yeast extract powder, 5.0 g; glucose, 20.0 g; dipotassium phosphate, 5.0 g; diammonium citrate, 2.0 g; sodium acetate, 5.0 g; magnesium sulfate heptahydrate, 0.5 g; manganese sulfate tetrahydrate, 0.2 g; Tween 80, 1.0 g; agar 15.0 g; distilled water 1000 mL, with a pH between 6.2 and 6.4 and sterilize at 121° C. for 15 minutes.

*L. paracasei* ET-22 is a micro-aerobic bacteria, which has better growth in a facultative anaerobic environment, produces lactic acid, has acid resistance, can survive in an acid environment of pH 2.5 and an environment of 0.4% bile salt for 4 hours, a mesophilic bacteria, with a growth temperature ranging of 15-45° C., and the optimal growth temperature of about 37° C.

Figure 1:
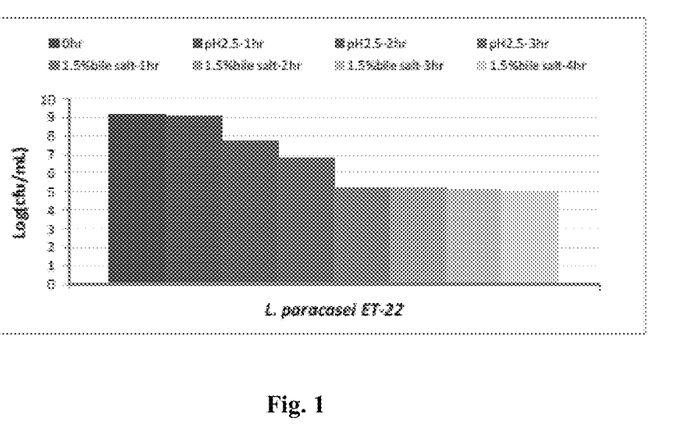
FIG. 1. Evaluation of the tolerance of *L. paracasei* ET-22 in a simulated intestinal environment, a gastric acid and bile salt environment.

Example 1: Tolerance to Artificial Gastric Fluid, Intestinal Fluid, Artificial Bile The *L. paracasei* ET-22 strain was activated three times and divided into 8 tubes. One tube was used for colonies counting to calculate the number of initial viable bacteria. The remaining seven tubes were centrifuged at 4000 rpm for 10 minutes, and after removing the supernatant, the cells were cultured in pH 2.5 medium at 37° C. for 1 to 3 hours. Every hour, one tube was centrifuged at 4000 rpm for 10 minutes, and after removing the supernatant, the pellet was washed twice with 5 mL RO water to calculate the number of viable bacteria. The remaining 4 tubes were centrifuged at 4000 rpm for 10 minutes after 3 hours, and after removing the supernatant (pH 2.5 MRS broth), the 4 tubes were mixed well with MRS broth with 1.5% bovine bile, then evenly distributed into 4 tubes, and incubated at 37° C. for 1-4 hour. Every hour, one tube was centrifuged at 4000 rpm for 10 minutes, and after removing the supernatant, the pellet was washed twice with 5 mL RO water to calculate the number of viable bacteria. The change of the numbers of viable bacteria measured at different times was compared and analyzed. The survival rate of the strains is shown in FIG. 1.

The results showed that, after continuous processing through acidic medium and bile salt environment, i.e., after 7 hours of continuous gastric acid and cholate treatment in a simulated digestive environment, *L. paracasei* ET-22 maintains the total number of bacteria to the 5th power, which proves that *L. paracasei* ET-22 can pass the strict test of the human digestive system environment.

Example 2. Intestinal Cell Adhesion

The cover glass was picked up with tweezers, sterilized on an alcohol lamp, and then placed in a 6-well plate for use.

Caco-2 cells were taken out from the preservation tube, and after adjustment, were transferred to the 6-well plate for culture until confluence, and then used in the test. During the test, the liquid in the plate was removed, and after washing twice with PBS buffer, 1.5 mL of bacterial suspension ($1 \times 10^9$ CFU/mL) and 1.5 mL of cell culture medium (containing 10% PBS and 1% penicilin-streptomycin) per well were added and mixed well. After culturing in a constant temperature incubator (37° C., 5% $CO_2$) for 4 hours, the plate was washed twice with sterile PBS, the cells were fixed with methanol, Gram stained, and the number of viable bacteria was counted under a microscope.

Figure 2:
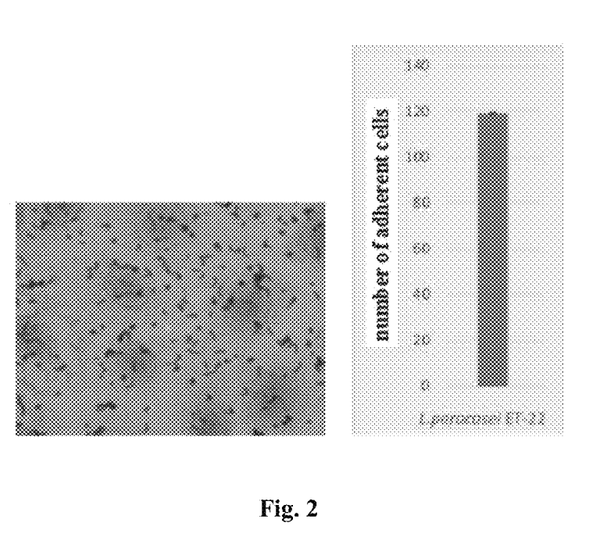
FIG. 2. Evaluation of the intestinal adhesion of *L. paracasei* ET-22.

The adhesion of the strain to Caco-2 cells was tested by an adhesion test. The results are shown in FIG. 2, which shows that *L. paracasei* ET-22 has strong adhesion to Caco-2 cells.

Example 3: Intestinal Flora Regulation Effect

This example is intended to confirm the effect of the *Lactobacillus paracasei* of the present disclosure for intestinal flora regulation.

36 healthy SPF BABL/c mice weighing 18-22 g (provided by Beijing Huafukang Biotechnology Co. Ltd.) were adaptively reared for 3 days, and then were randomly divided into 3 groups, namely the blank control group and the test groups, each with 12 mice. Animals in each test group were administered by gavage with sterile water dissolved with *Bifidobacterium lactis* BL-99 powder (gavage volume 0.2 mL/10 g), once a day for continuous 14 days, and the blank control group was given the same volume of sterile water. Intragastric dose: $1.3 \times 10^7$ CFU/ml (calculated according to the human body dose of $2 \times 10^9$ CFU/day, with a conversion factor between human and mouse of 0.0026). Centrifuge tubes were sterilized, numbered, and filled with feces of mice collected under aseptic conditions after adaptive feeding, 2-3 pellets, about 100 mg, per tube. The tubes were then transferred to the sterile operation room at a low temperature for intestinal flora detection. At the end of the experiment, mouse feces were collected again. After grouping and numbering the mice with picric acid, the mice were weighed on the 8th and 14th days of administration of the test substance, respectively, and the gavage amount of the mice was calculated. The mice were weighed once at the end of the experiment. Colonies counting: Selective medium was prepared according to the strain to be identified. The strain to be tested and the corresponding medium are shown in the table below. The culture medium was sterilized, shaken well, cooled to 45° C.-50° C., poured into the plate for use.

TABLE 3

Strains to be tested and corresponding selective media

| Strains to be tested | Selective media |
| --- | --- |
| *Enterobacter* | Eosin Methylene Blue (EMB) Agar |
| *Bifidobacterium* | BBL agar |
| *Lactobacillus* | LBS agar |

The collected mouse feces were placed in a sterile tube containing 0.5 mL of physiological saline to prepare a bacterial suspension. The suspension was shaken for 1 min before use. 0.1 mL of the bacterial suspension was pipetted with a 0.1 mL micropipette and slowly injected into 0.9 mL of sterile physiological saline, shaken or repeatedly pipetted to mix well to prepare a 1:10 bacterial suspension, which was then serially diluted 10 times in a similar manner with another 0.1 mL micropipette, until $10^{-7}$ g/ml concentration. According to the number of viable bacteria to be identified, two consecutive appropriate dilutions were selected. 10 μL of bacterial suspension of each dilution was pipetted with a 0.1 mL micropipette and surface-coated on selective agar plates, and cultured under the culture conditions indicated in the below table. The colonies counting was carried out with reference to the "GB 4789.2-2010 National Food Safety Standard Food Microbiology Examination: Aerobic Plate Count"

TABLE 4

Culture media and identification methods for intestinal flora

| Item | Media | Culture condition |
| --- | --- | --- |
| *Enterobacter* | Eosin Methylene Blue Agar | 36° C. ± 1° C. for 24 h |
| *Bifidobacterium* | BBL agar | 36° C. ± 1° C. for 48 h, anaerobic |
| *Lactobacillus* | LBS agar | 36° C. ± 1° C. for 48 h |

SPSS17.0 was used for data statistics. The changes in bifidobacteria, lactic acid bacteria, and enterobacteria within and between groups before and after the experiment were compared.

The results of animal weight changes during the experiment are shown in Table 5 below. During the experimental period, the animals were characterized as normal, and no adverse reactions occurred after the administration of the test substance. During the experimental period, there was no significant difference in the weight between the two groups of animals. It can be seen from Tables 6-8 that *Lactobacillus paracasei* ET-22 can significantly promote the growth of *Bifidobacterium* and *Lactobacillus*, and has no significant effect on *Enterobacter*. According to the comparison before and after the intervention within the group, the effect of ET-22 is significantly higher than that of the well-known strain *Lactobacillus casei* LC-01 (DSM 19465), and thus has an excellent effect.

Figure 3:
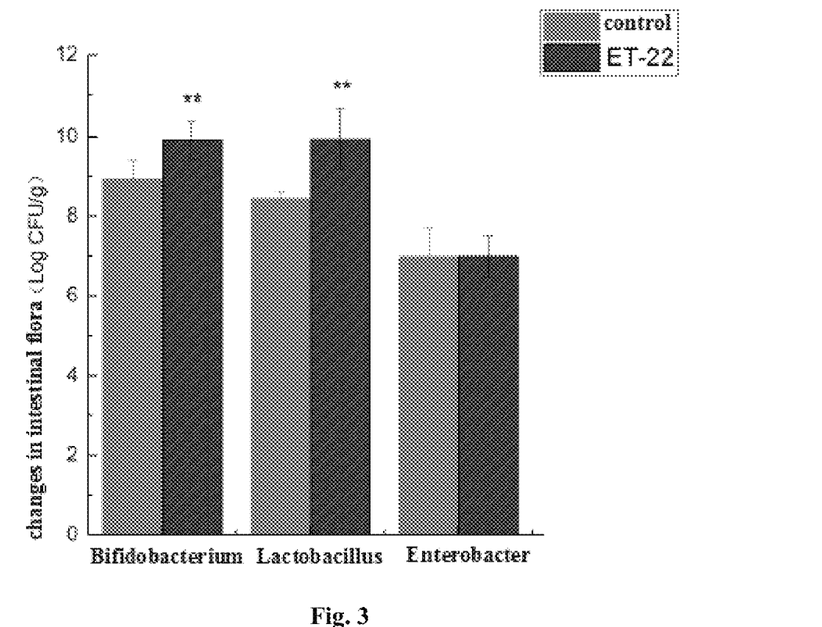
FIG. 3. Regulation of intestinal flora by *L. paracasei* ET-22.

Therefore, in this study, *Lactobacillus paracasei* ET-22 has the effect of regulating intestinal flora (FIG. 3).

TABLE 5 change of animal weight

| Group | number of animals | Initial weight (g) | Mid-term weight (g) | Final weight (g) |
| --- | --- | --- | --- | --- |
| Control group | 14 | 21.89 ± 1.25 | 22.14 ± 0.87 | 21.24 ± 0.87 |
| L. casei LC-01 | 14 | 22.46 ± 1.12 | 22.83 ± 1.04 | 22.03 ± 1.73 |
| L. paracasei ET-22 | 14 | 21.90 ± 1.50 | 21.42 ± 1.08 | 19.38 ± 1.66 |

TABLE 5 change of numbers of animal intestinal bifidobacteria (LgCFU/g) before and after the test

| Group | No. of animals | before intervention | after intervention | P value before and after intervention | P value after intervention compared with the control group |
| --- | --- | --- | --- | --- | --- |
| Control group | 14 | 8.66± 0.57 | 8.94± 0.46 | 0.196 | |

TABLE 5-continued change of numbers of animal intestinal bifidobacteria
(LgCFU/g) before and after the test

| Group | No. of animals | before intervention | after intervention | P value before and after intervention | P value after intervention compared with the control group |
|---|---|---|---|---|---|
| L. casei LC-01 | 14 | 8.94± 0.50 | 9.70 ± 0.56** | 0.001 | 0.003 |
| L. paracasei ET-22 | 14 | 8.67± 0.59 | 9.91 ± 0.46** | 0.000 | 0.000 |

Figure 4:
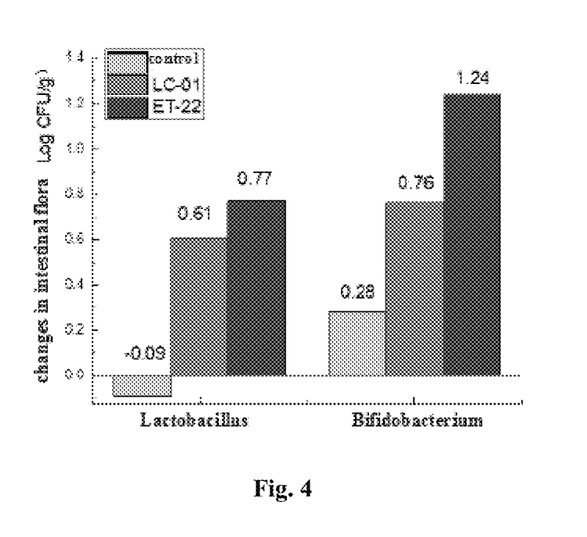
FIG. 4. Comparison of the regulation of intestinal flora by *L. paracasei* ET-22 and *Lactobacillus casei* LC-01.

The results showed that the increase rate of the ET-22 group after the intervention was significantly higher than that of the well-known strain LC-01: the number of bifidobacteria was increased by 1.24 orders of magnitude for the ET-22 group, and 0.76 orders of magnitude for the LC-01 group (FIG. 4). ET-22 belongs to a *Lactobacillus* genus, but it can significantly increase the number of *Bifidobacterium* genus by more than one order of magnitude, higher than that of LC-01, showing that ET-22 has extremely strong ability to increase intestinal bacteria.

TABLE 7 change of numbers of animal Lactobacillus
(LgCFU/g) before and after the test

| Group | No. of animals | before intervention | after intervention | P value before and after intervention | P value after intervention compared with the control group |
|---|---|---|---|---|---|
| Control group | 14 | 8.54± 0.57 | 8.45 ± 0.18 | 0.566 | |
| L. casei LC-01 | 14 | 8.96± 0.62 | 9.57 ± 0.57** | 0.000 | 0.000 |
| L. paracasei ET-22 | 14 | 9.17± 0.91 | 9.94 ± 0.77** | 0.000 | 0.000 |

The results showed that the increase rate of the ET-22 group after the intervention was significantly higher than that of the well-known strain LC-01: the number of *Lactobacillus* was increased by 0.77 orders of magnitude for the ET-22 group, and 0.61 orders of magnitude for the LC-01 group (FIG. 4).

TABLE 8

Numbers of animal Enterobacter (LgCFU/g) before and after the test

| Group | No. of animals | before intervention | after intervention | P value before and after intervention | P value compared with the control group after intervention |
|---|---|---|---|---|---|
| Control group | 14 | 6.48 ± 0.32 | 6.98 ± 0.74 | 0.123 | |
| L. casei LC-01 | 14 | 6.71 ± 0.68 | 6.97 ± 0.40 | 0.071 | 0.423 |
| L. paracasei ET-22 | 14 | 6.84 ± 0.66 | 6.98 ± 0.52 | 0.119 | 0.239 |

Example 4: Intestinal Flora Regulation Effect (Sequencing Result)

This example is intended to confirm the effect of *Lactobacillus paracasei* of the present disclosure in intestinal flora regulation. For the principles and procedures, please refer to "Technical Specifications for Inspection and Evaluation of Health Foods-Judgment Criteria for Regulating Intestinal Flora Function". The difference between this Example and Example 3 is that this experiment uses 16S rDNA sequencing results.

Experimental samples: Bacterial powder samples (see packaging specifications for the number of live bacteria) were provided by Inner Mongolia Dairy Technology Research Institute Co., Ltd.

Experimental material: 182 healthy adult 6-week-old BABL/c mice weighing approximately 18-20 g.

Experimental Procedure

1. Sample Preparation

Live bacteria samples (ET-22): According to the sample specifications, 1 g of each live bacteria sample was weighed and suspended to 40 ml in PBS solution, to obtain a concentration of live bacteria of $2.5 \times 10^9$ CFU/ml.

High-dose group: Based on the gavage amount of 0.2 ml/10 g mice, the amount for a mouse weighting 20 g was 0.4 ml. The gavage dose for mice in the high-dose group was $10^9$ CFU/20 g.

Medium-dose group: 5 ml of the high-dose suspension was added to PBS to make up to 50 ml. Based on the gavage amount of 0.2 ml/10 g mice, the amount for a mouse weighting 20 g was 0.4 ml. The gavage dose for mice in the medium-dose group was $10^8$ CFU/20 g.

Low-dose group: 5 ml of the medium-dose suspension was added to PBS to make up to 50 ml. Based on the gavage amount of 0.2 ml/10 g mice, the amount for a mouse weighting 20 g was 0.4 ml. The gavage dose for mice in the medium-dose group was $10^7$ CFU/20 g.

2. Regulation of Intestinal Flora (1) 6 week-old BABL/c mice were housed in a clean-grade animal room with a temperature of 22° C., a humidity of 10-60%, alternating 12 hours of light and dark, standard feed feeding, and free access to water.

(2) After adaptive feeding for 5 days, 182 mice were randomly divided into 13 groups, with 14 mice in each group. See Table 9 for grouping conditions.

TABLE 9

Experimental grouping for regulating intestinal flora

| Group | Samples | number of animals (n) | gavage dose (calculated by human daily intake, cfu/d) |
|---|---|---|---|
| Control group | PBS | 14 | — |
| ET-22 low-dose group | ET-22 live bacteria samples | 14 | $3.88 \times 10^9$ |
| ET-22 medium-dose group | ET-22 live bacteria samples | 14 | $3.88 \times 10^{10}$ |
| ET-22 high-dose group | ET-22 live bacteria samples | 14 | $3.88 \times 10^{11}$ |

(3) Before starting the gavage, the feces of each mouse were collected under aseptic conditions, labeled, and stored at −20° C. for detection of intestinal flora.

(4) In the experiment, each test substance was given by gavage administration of 0.2 ml/10 g. The control group was given PBS on days 1-14, and the test groups were given the corresponding dose of test substance by gavage according to Table 9 respectively. Mice were weighed once a week, and the amount of gavage was adjusted according to the body weight.

(5) After 14 days, the feces of each mouse were collected under aseptic conditions, labeled, and stored at −20° C. for detection of intestinal flora.

3. Changes of Microbial Diversity in the Intestine of Mice

Microbial diversity was determined based on the Illumina HiSeq sequencing platform, using the paired-end sequencing (Paired-End) method to construct a library of small fragments for sequencing. Species composition of the sample can be revealed by splicing and filtering of Reads, OTUs (Operational Taxonomic Units) clustering, and species annotation and abundance analysis; the optimized sequence was clustered, divided into OTU, and the species classification was obtained according to the sequence composition of OTU. Based on the OTU analysis results, taxonomic analysis was performed on the samples at various classification levels to obtain the community structure of each sample at the genus level.

Alpha diversity analysis was used to study the species diversity within a single sample. The Ace, Chao1, Shannon, and Simpson indexes of each sample at the 97% similarity level were counted, and the sample dilution curve and grade abundance curve were drawn; Alpha Diversity, Beta Diversity, and significant species difference analysis were further carried out to discover differences between samples. Comparison of intestinal flora alpha diversity index: Chao1 and ACE index measure species abundance, that is, the number of species; Shannon and Simpson index are used to measure species diversity, and are affected by species abundance and species uniformity in the sample community. Under the same species abundance, the greater species uniformity in the community, the greater the diversity of the community. The larger the Shannon index value and the smaller the Simpson index value, the higher the species diversity of the sample. Compared with the control group in the genus level, the ET-22 intervention can significantly increase the relative abundance in the intestine of mice. The OTU, ACE, and Chao1 indexes of the low-dose group increased significantly, showing that the low-dose ET-22 can most significantly increase the intestinal microbial diversity.

TABLE 10

Intestinal microbial diversity of mice

| Group | Before intervention | | | | | After intervention | | | | |
|---|---|---|---|---|---|---|---|---|---|---|
| | OTU | ACE | Chao1 | Simpson | Shannon | OTU | ACE | Chao1 | Simpson | Shannon |
| Control group | 294.50± 21.52 | 311.92± 20.16 | 316.19± 20.04 | 0.08± 0.03 | 3.46± 0.18 | 303.67± 24.71 | 323.29± 23.3 | 369.52± 24.96 | 0.04± 0.01 | 3.43± 0.19 |
| ET22 low-dose group | 300.00± 25.75 | 319.73± 23.81 | 322.82± 25.23 | 0.06± 0.02 | 3.65± 0.29 | 349.83± 22.63 | 370.05± 19.97 | 374.87± 22.53 | 0.05± 0.01 | 3.96± 0.22 |
| ET22 medium-dose group | 286.25± 32.90 | 309.35± 30.25 | 314.09± 31.48 | 0.1 ± 0.04 | 3.26± 0.37 | 328.58± 43.62 | 353.35± 40.35 | 362.58± 39.74 | 0.07± 0.06 | 3.72± 0.48 |
| ET22 high-dose group | 292.16± 39.34 | 315.04± 38.49 | 317.05± 39.67 | 0.09± 0.06 | 3.41± 0.55 | 319.83± 45.74 | 337.6 ± 41.48 | 343.34± 42.91 | 0.06± 0.04 | 3.78± 0.4 |

TABLE 11

Test results at genus levels after ET-22 intervention (%)

| Genus | Control group | ET22 low-dose group | ET22 medium-dose group | ET22 higjh-dose group |
|---|---|---|---|---|
| *Desulfovibrio* | 2.1391 ± 0.5097 | 1.3084 ± 0.4245 | 1.1237 ± 0.5559 | 1.6218 ± 0.8902 |
| *Enterorhabdus* | 0.3447 ± 0.0971 | 0.2563 ± 0.1022 | 0.3013 ± 0.1801 | 0.2298 ± 0.1687 |
| *Helicobacter* | 0.1254 ± 0.0492 | 0.2174 ± 0.6786 | 0.0748 ± 0.0267 | 0.06 ± 0.0288 |
| *Coprococcus_1* | 0.0795 ± 0.0126 | 0.0785 ± 0.0507 | 0.1009 ± 0.0734 | 0.0802 ± 0.0649 |
| *Escherichia-Shigella* | 0.0281 ± 0.0054 | 0.0045 ± 0.0025 | 0.0036 ± 0.0022 | 0.0011 ± 0.0010 |
| *Enterococcus* | 0.0158 ± 0.0067 | 0.005 ± 0.0018 | 0.001 ± 0.0011 | 0.0004 ± 0.0009 |
| *Akkermansia* | 0.0009 ± 0.0022 | 2.1671 ± 4.8421 | 2.5336 ± 8.4747 | 0.001 ± 0.0026 | underlined: statistically significant difference compared to the control group (p < 0.05).

At the level of the pathogenic genus, compared with the control group, *Desulfovibrio* in the intestinal tract of mice in both the low-dose and the medium-dose ET-22 groups was significantly reduced; the numbers of *Helicobacter* in the middle-dose and high-dose groups were significantly reduced; *Escherichia-Shigella* of the three groups of low-dose and middle-dose decreased significantly. BL-99 can significantly increase the relative abundance of *Lactobacillus* in the intestine of mice, and the BL-99 low-dose group leads to the most significant increase in *Lactobacillus*.

Therefore, supplementing with different doses of ET-22 can adjust the balance of intestinal flora, inhibit the number of harmful bacteria and even pathogenic bacteria, and play a potential health effect.

Example 5: Analysis of Immunomodulatory Activity

5.1 Humoral Immunity Test 5.1.1 Antibody-Producing Cell Detection Experiment The spleen cell suspension of mice immunized with sheep red blood cells (SRBC) was mixed with a certain amount of SRBC. With the participation of complement, the SRBCs around the antibody-producing spleen cells were dissolved to form plaques visible to the naked eye. The number of hemolytic plaques can reflect the number of antibody-producing cells.

The PBS suspension was used to adjust the concentration of live bacterial samples according to different gavage amounts before the animals were gavaged (the dosage was about $10^7$-$10^9$ CFU/day). After 28 consecutive days of administering to the animals, each mouse was immunized by intraperitoneal injection of 0.2 mL of SRBC. The mice were sacrificed 4 days after SRBC immunization, and the spleen was collected to prepare a cell suspension of $5 \times 10^6$ cells/mL. After heating to dissolve, agarose was mixed with an equal amount of double Hank's solution, and divided into small test tubes, 0.5 mL per tube. Then 50 μL of 20% (V/V, packed cell volume, in physiological saline) SRBC, and 200 μL of spleen cell suspension were added to the tube, mixed quickly, and poured onto a six-well plate with a thin layer of agarose. After solidification of the agar, the plate was placed in a carbon dioxide incubator and incubated for 1 h, then complement diluted in SA buffer (1:10) was added, incubated for 2 h, and then the number of hemolytic plaques was counted.

Figure 5:
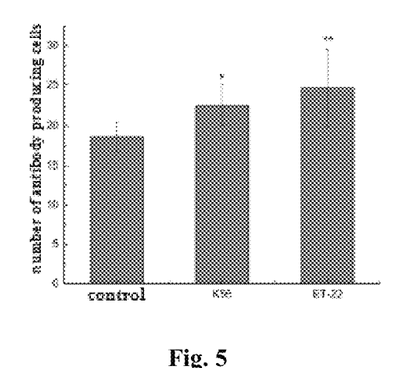
FIG. 5. The number of antibody-producing cells by *L. paracasei* ET-22.

The results of the number of antibody-producing cells are shown in FIG. 5. Compared with the control group, *L. paracasei* ET-22 and *L. paracasei* K56 (CGMCC 15139) significantly increased the number of antibody-producing cells ($p<0.05$).

5.1.2 Determination of Serum Hemolysin Half Hemolysis Concentration ($HC_{50}$)

After 28 consecutive days of administration to the animals, each mouse was immunized by intraperitoneal injection of 0.2 mL of SRBC. After 4 days, the eyeballs were removed and blood was collected in a 1.5 mL centrifuge tube, and placed at 4° C. for about 1 hour to allow serum full released. The tube was centrifuged at 2000 r/min for 10 minutes to collect the serum. The serum was diluted 100 times with SA buffer. The diluted serum was added to a 96-well plate, 100 μL per well, and then 50 μL of 10% (v/v) SRBC, and 100 μL of complement (diluted 1:8 with SA solution) were added sequentially. The plate was placed in a constant temperature water bath at 37° C. for 30 min, and centrifuged at 1500 r/min for 10 min. 50 μL of supernatant from each sample well and blank control well was added to another 96-well culture plate, and 150 μL of Venchi's reagent was added. In addition, a half hemolysis well was set up, into which 12.5 μL of 10% (v/v) SRBC and then 2000 μL of Venchi's reagent were added. The plate was thoroughly mixed in the shaking period, and after placing for 10 minutes, the optical density value of each well was measured with an automatic microplate reader at 540 nm.

The amount of hemolysin is expressed as the half hemolysis concentration ($HC_{50}$), calculated according to the following formula:

$$HC_{50} \text{ of the sample} = \text{Optical density of the sample} / \text{Optical density at SRBC half hemolysis} \times \text{Dilution factor}$$

Figure 6:
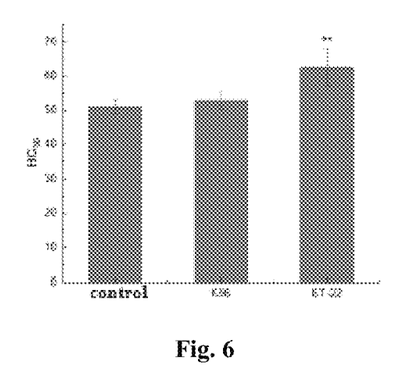
FIG. 6. The serum hemolysin half hemolysis concentration ($HC_{50}$) by *L. paracasei* ET-22.

It can be seen from FIG. 6 that the half hemolysis concentration $HC_{50}$ of the *L. paracasei* ET-22 group is significantly higher ($p<0.05$) that of the control group, and higher than that of the *L. paracasei* K56.

5.2 NK Cell Activity Test

After 28 consecutive days of administration to the animals, the target cells YAC-1 were subcultured 24 hours before the start of the experiment, washed twice with Hank's solution, and the cell concentration was adjusted before use to $1 \times 10^5$ cells/ml (target cells) with RPMI 1640 complete culture medium containing 10% calf serum. The mice were sacrificed by cervical dislocation, and the spleen was removed aseptically to prepare a spleen cell suspension. The suspension was washed twice with Hank's solution and centrifuged at 1000 rpm for 10 min. The pellet was resuspended in 2 mL of RPMI 1640 complete medium containing 10% calf serum, stained with trypan blue for counting (the number of live cells should be above 95%), and the cell concentration was adjusted to $1 \times 10^7$ cells/mL (effector cells), so that the effector-target ratio was 100:1. 100 μL of target cells and 100 μL of effector cells were added to the U-shaped bottom 96-well culture plate, 100 μL of target cells and 100 μL of culture medium were added to the natural release wells of target cells, and 100 μL of target cells and 100 μL of 1% NP40 were added to the maximum release wells of target cells, all of the above were provided with three parallel wells. The 96-well culture plate was incubated in a 37° C., 5% $CO_2$ incubator for 4 hours, and centrifuged at 1500 rpm for 5 minutes. 100 μL of the supernatant from each well was pipetted into a flat-bottomed 96-well culture plate, and 100 μL of LDH matrix solution was added to react for 3 minutes, and then 30 μL of 1 mol/L HCL solution was added to each well to stop the reaction. The OD value was measured at 490 nm on a microplate reader and the NK activity was calculated as follows:

$$NK \text{ cell activity} = (\text{reaction well } OD - \text{natural release well } OD)/(\text{maximum release well } OD - \text{natural release well } OD) \times 100\%$$

Figure 7:
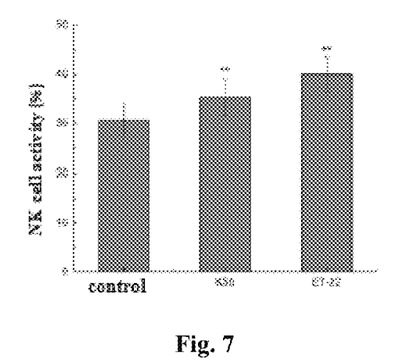
FIG. 7. The activity of NK cell by *L. paracasei* ET-22.

It can be seen from FIG. 7 that *L. paracasei* ET-22 has higher ability to activate NK cell activity than L. paracaset K56, and the difference from the control group is significant ($p<0.05$).

It can be seen from the experimental results that, since the *L. paracasei* ET-22 antibody-producing cell test and the half hemolysis concentration $HC_{50}$ result were positive, the humoral immunity of the sample *L. paracasei* ET-22 is determined to be positive; since the NK cell activity test result was positive, it can be determined that the NK cell activity test of the sample *L. paracasei* ET-22 is positive. In summary, *L. paracasei* ET-22 can be considered to have the effect of enhancing immunity.

L. paracasei ET-22 Inhibits Oral Pathogens

At present, it is known that some strains are effective in inhibiting caries bacteria and periodontal bacteria. However, the literature indicates that most studies were conducted on the efficacy of individual strains in the oral cavity, and not all test results prove that lactic acid bacteria are helpful for oral health, and there are individual differences in the efficacy of strains (Anna Haukioja, European Journal of Dentistry 2010 (4): 348-355). For example, Vuotto C et al. (International Journal of Oral Science 2014 (6): 189-194) analyzed the inhibitory ability of probiotics against pathogenic bacteria, and pointed out that the result for any one probiotic strain will not be the same, and even for different probiotic strains of the same species, the test results are sometimes opposite. This result emphasizes that the efficacy of probiotics in inhibiting oral pathogens and whitening teeth is indeed a strain-specific phenomenon.

In fact, as can be seen from the following test results of the present disclosure, most Lactobacillus strains do not have the effect of inhibiting oral pathogens and whitening teeth. The current domestic and foreign literature reports on the research of probiotics in maintaining oral health-related functions have only recently increased. In the early days, it was thought that the genus of lactic acid bacteria in probiotics may coexist with oral pathogens due to the acid-generating properties, and they may also cause corrosion of enamel and caries. However, in fact, experiments have shown that lactic acid bacteria can not only inhibit dental caries and periodontal bacteria, but also compete with them for the living space of oral mucosa and nutritional source, and cause the aggregation of oral pathogens and thus easy to be excluded. But these characteristics must be confirmed through experiments, and not all strains have the same characteristics and experimental results.

Example 6: Analysis of the Characteristics of the Strain to Produce Hydrogen Peroxide to Confirm the Function of Teeth Whitening The ability of the lactic acid bacteria strain of the present disclosure—Lactobacillus paracasei ET-22 strain to produce hydrogen peroxide was examined to verify the ability of the lactic acid bacteria strain of the present disclosure to whiten teeth. The experimental steps were as follows:

1. A plate for screening hydrogen peroxide producing probiotics was prepared;
2. 0.25 mg/mL of Trimethylborane TMB and 0.01 mg/mL of Horseradish Peroxidase HRP were added to the plate';
3. The plate was divided into four partitions for cultivating target strains;
4. After incubation for two days, if there was a lactic acid bacteria strain that produced hydrogen peroxide, the surrounding area of the colonies would appear blue;
5. The concentration of hydrogen peroxide in the lactic acid bacteria and secondary metabolites was determined using hydrogen peroxide test paper;
6. The lactic acid bacteria liquid was cultured and centrifuged at 4500 rpm for 5 minutes;
7. A fraction of the bacterial cells was dissolved in 4.9 ml of 100 mM Piperazine-1,4-bisethanesulfonicacid (PIPES); and
8. The culture was incubated at 37° C. for 5 hours and centrifuged at 220 rpm. 10 microliters (μL) of the supernatant or sedimented bacterial cells were dropped in a hydrogen peroxide test paper (Merck) and reacted for 10 seconds. The color change was observed and compared with a colorimetric card to record the concentration.

Figure 8:
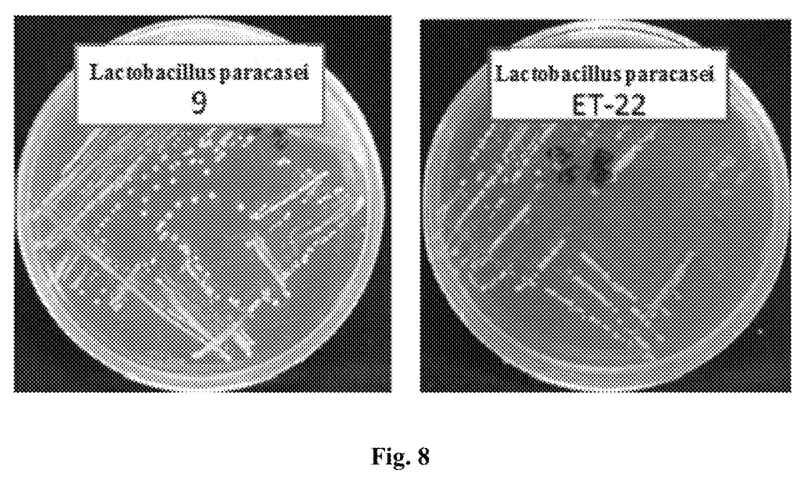
FIG. 8. Test results of the production of hydrogen peroxide by *L. paracasei* ET-22.

The experimental results are shown in FIG. 8. FIG. 8 shows the results of the ability of the Lactobacillus paracasei ET-22 strain to secrete hydrogen peroxide on the plate after culturing on the hydrogen peroxide detection plate.

It can be seen from the test results in FIG. 8 that after two days of cultivation, the Lactobacillus paracasei ET-22 strain of the present disclosure secreted hydrogen peroxide well during the growth of the strain. It should also be noted that other lactic acid bacteria strains of the same species other than the strain of the present disclosure, such as Lactobacillus paracasei strain 9 (BCRC16093), have no ability of secreting hydrogen peroxide, as shown in FIG. 8.

Example 7: Inhibition of Oral Pathogens by Active Lactic Acid Bacteria for Maintaining Oral Health In order to exert the oral health function of lactic acid bacteria, the resistance of oral pathogens is the most important. In addition to the well-known Streptococcus mutans, oral pathogens also include Fusobacterium nucleatum subsp. polymorphum, Aggregatibacter actinomycetemcomitans, and Porphyromonas gingivalis, etc. These strains may cause several symptoms, for example, Streptococcus mutans causes caries; Fusobacterium nucleatum subsp. polymorphum mainly causes periodontal disease, halitosis and colon cancer; Aggregatibacter actinomycetemcomitans is the main bacterial species causing periodontitis, oral inflammation and pneumonia; and Porphyromonas gingivalis is the main cause of adult periodontitis and halitosis. In addition, for oral odor, in addition to Porphyromonas gingivalis as the main bacteria causing halitosis, Fusobacterium nucleatum subsp. polymorphum, Aggregatibacter actinomycetemcomitans and Porphyromonas gingivalis all produce sulfide, and are the main bacterial species that affect oral odor.

Therefore, the present disclosure conducted a pathogenic bacteria inhibition test to evaluate the ability of the active Lactobacillus paracasei ET-22 strain of the present disclosure to inhibit oral pathogenic bacteria, thereby achieving the effect of maintaining oral health. The experimental steps were as follows:

1. The active lactic acid bacteria was applied to the center of the MRS plate with a diameter of two centimeters and cultured for two days;
2. The culture medium for oral pathogens was poured on the plate where the lactic acid bacteria had grown, and after solidification, the high concentration of oral pathogens were evenly spread on the pathogen culture plate;
3. The plate was incubated at 37° C. for 2-4 days; and
4. The inhibition diameter was measured if the growth of pathogenic bacteria was inhibited in the central part where the lower medium was coated with lactic acid bacteria.

Figure 9:
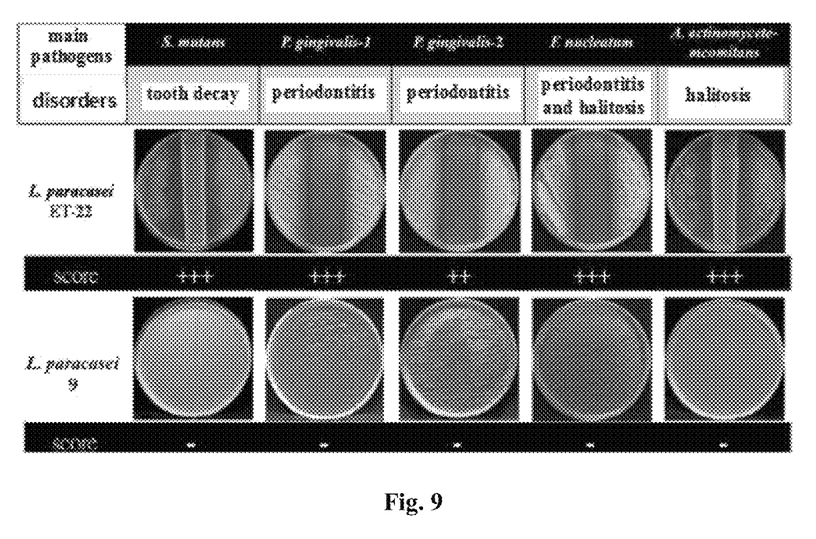
FIG. 9. Test results of inhibiting oral pathogens by *L. paracasei* ET-22.

The experimental results are shown in FIG. 9, which shows the analysis of the ability of the lactic acid bacteria strain of the present disclosure to inhibit oral pathogens.

FIG. 9 shows the results of the Lactobacillus paracasei ET-22 strain of the present disclosure in inhibiting the survival of oral pathogens. Compared with another strain of Lactobacillus paracasei 9, the inhibitory effect of ET-22 is more significant.

Example 8: Inhibition of Oral Pathogens by Deactivated Lactic Acid Bacteria for Maintaining Oral Health In addition to the function of active lactic acid bacteria to inhibit oral pathogenic bacteria, it is unclear whether the deactivated lactic acid bacteria have the function of inhibiting oral pathogenic bacteria. Therefore, a pathogen inhibition test was conducted to evaluate the ability of the inactivated *Lactobacillus paracasei* ET-22 strain of the present disclosure to inhibit oral pathogens, thereby achieving the effect of maintaining oral health. The experimental steps were as follows:

1. Oral pathogens were activated;
2. The number of heat-killed lactic acid bacteria was adjusted and the bacteria were added to co-culture with the pathogenic bacteria according to the ratio of one billion bacteria per milliliter;
3. The bacteria were incubated in an anaerobic manner at 150 rpm in a 37° C. environment for 2-4 days; and
4. The number of pathogenic bacteria was counted.

Figure 10:
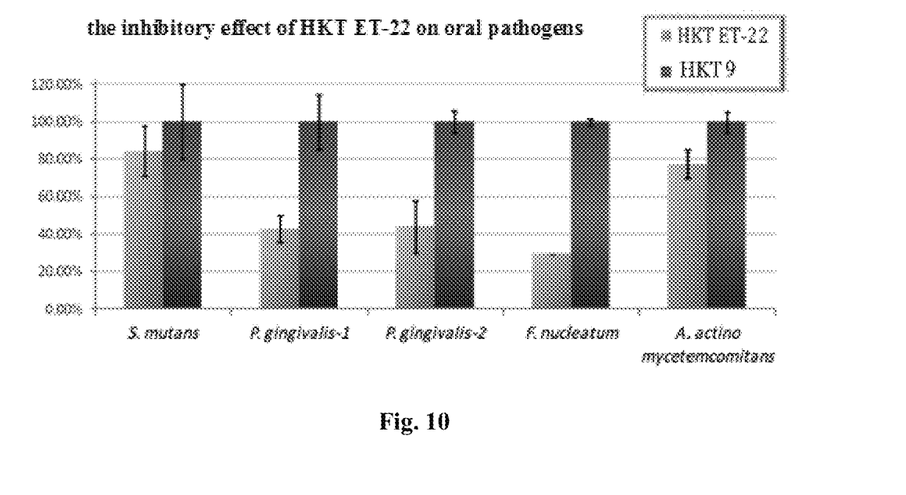
FIG. 10. Test results of inhibiting oral pathogens by deactivated *L. paracasei* ET-22 strain.

The experimental results are shown in FIG. 10, which is an analysis of the ability of the deactivated lactic acid bacteria strain of the present disclosure to inhibit oral pathogens; the histograms are all expressed in Mean±SD and compared with another strain of *Lactobacillus paracasei* 9.

FIG. 10 shows the results of the deactivated *Lactobacillus paracasei* ET-22 strain of the present disclosure in inhibiting the survival of oral pathogens. Compared with the inhibitory effect of the *Lactobacillus paracasei* 9 strain, ET-22 is more remarkable.

Based on the above test results, the food composition and pharmaceutical composition containing the lactic acid bacteria strain of the present disclosure can inhibit the growth of oral pathogenic bacteria, and can be used for reducing human caries, periodontal disease and breath odor. Preferably, the strain of lactic acid bacteria that can secrete hydrogen peroxide also has the ability to whiten teeth. The present disclosure found lactic acid bacteria that have no side effects on the human body and are beneficial to maintaining oral health as a new option for maintaining oral health.

Unless otherwise stated, all numbers used in this specification (including claims) to indicate the amount of components, cell culture, processing conditions, etc. should be understood to be modified by the term "about" under all conditions. Therefore, unless otherwise stated to the contrary, the numerical parameters are approximate and may vary according to the desired characteristics sought to be obtained by the present disclosure. Unless otherwise stated, the term "at least" before a series of elements should be understood to refer to every element in the series. Those skilled in the art will recognize or be able to determine with no more than routine experimentation many equivalents of the specific embodiments of the invention described herein. The appended claims are intended to cover such equivalents.

Those skilled in the art will understand that many modifications and variations of the present disclosure can be made without departing from the spirit and scope thereof. The specific embodiments described herein are provided by way of example only, and are not meant to be limiting in any way. The true scope and spirit of the present disclosure are shown by the appended claims, and the description and embodiments are merely exemplary.

The above-mentioned examples are only to illustrate the technical ideas and features of the present disclosure, and their purpose is to enable those skilled in the art to understand the content of the present disclosure and implement it accordingly, but not to limit the patent scope of the present disclosure, that is, changes or modifications made according to the spirit of the present disclosure should still be covered by the patent scope of the present disclosure.

What is claimed is:

1. A method for treating a subject, comprising administering an effective amount of *Lactobacillus paracasei* ET-22 strain to a subject in need thereof for 1) whitening teeth and/or inhibiting oral pathogens; 2) adjusting balance of flora in the subject; 3) promoting growth of bifidobacteria and/or lactic acid bacteria; and/or 4) enhancing immunity of the subject.

2. The method of claim 1, wherein the ET-22 strain is in a form of a composition which comprises the ET-22 strain, an excipient, a diluent and/or a carrier.

3. The method of claim 1, wherein the ET-22 strain is an active strain and/or a deactivated strain.

4. The method of claim 1, wherein the ET-22 strain is administered to a mammalian subject via a gastrointestinal route.

5. The method of claim 1, wherein the ET-22 strain is administered to the subject in an amount of equal to or more than $10^6$ CFU.

6. The method of claim 1, wherein the effective amount of the *Lactobacillus paracasei* ET-22 strain is administered to the subject further for enhancing humoral immunity and/or cellular immunity of the subject, increasing the number of antibody-producing cells, increasing half hemolysis concentration $HC_{50}$, and/or increasing activity of NK cells.

7. The method of claim 1, wherein the ET-22 strain is administered to the subject in an amount of equal to or more than $10^7$ CFU.

8. The method of claim 1, wherein the ET-22 strain is administered to the subject in an amount of equal to or more than $10^8$ CFU.

9. The method of claim 1, wherein the ET-22 strain is administered to the subject in an amount of equal to or more than $10^{10}$ CFU.

10. The method of claim 1, wherein the ET-22 strain is administered to the subject in an amount of equal to or more than $10^{11}$ CFU.

11. The method of claim 2, wherein the composition is a food composition, a pharmaceutical composition, or an oral cleaning composition.

12. The method of claim 11, wherein the composition is a food composition, and wherein the excipient, diluent and/or carrier is dairy drinks, tea, coffee, chewing gum and dentifrice, jerky for pet food or a combination thereof.

13. The method of claim 11, wherein the composition is an oral cleaning composition, and wherein the excipient, diluent and/or carrier is toothpaste, tooth powder, mouthwash, breath freshener spray, fluorine-coating agent, denture cleaner, pet tooth cleaning gum or pet laxatone, tooth brush, interdental brush, dental floss, oral swab or pet tooth cleaning bone.

14. The method of claim 11, wherein the composition is a pharmaceutical composition, which 1) is formulated an oral dosage form; 2) includes a therapeutic and/or prophylactic composition; 3) includes a nutritional composition; 4) is a dry or wet preparation; or 5) is formulated into a gel, cream, spray, aerosol, ointment, emulsion, suspension, patch, buccal tablet or sublingual tablet.

* * * * *